(12) United States Patent
Jenkins

(10) Patent No.: US 8,137,310 B2
(45) Date of Patent: Mar. 20, 2012

(54) SYRINGE HUB

(76) Inventor: David Howell Jenkins, Cheltenham (GB)

( * ) Notice: Subject to any disclaimer, the term of this patent is extended or adjusted under 35 U.S.C. 154(b) by 0 days.

(21) Appl. No.: 12/795,938

(22) Filed: Jun. 8, 2010

(65) Prior Publication Data

US 2010/0318030 A1     Dec. 16, 2010

(30) Foreign Application Priority Data

Jun. 11, 2009   (GB) .................................. 0909985.4

(51) Int. Cl.
*A61M 5/00*     (2006.01)
(52) U.S. Cl. ........................................................ 604/110
(58) Field of Classification Search .................. 604/110, 604/240, 245
See application file for complete search history.

(56) References Cited

U.S. PATENT DOCUMENTS

| | | | |
|---|---|---|---|
| 2,880,725 A * | 4/1959 | Kendall | 604/196 |
| 4,233,975 A | 11/1980 | Yerman | |
| 4,747,830 A * | 5/1988 | Gloyer et al. | 604/110 |
| 5,045,063 A | 9/1991 | Spielberg | |
| 5,254,093 A * | 10/1993 | Bartlett et al. | 604/110 |
| 5,688,240 A * | 11/1997 | Novacek et al. | 604/110 |
| 6,033,386 A * | 3/2000 | Novacek et al. | 604/195 |
| 6,368,306 B1 * | 4/2002 | Koska | 604/218 |

FOREIGN PATENT DOCUMENTS

| | | |
|---|---|---|
| GB | 2243552 | 6/1991 |
| WO | 9112038 | 8/1991 |
| WO | 9806447 | 2/1998 |

OTHER PUBLICATIONS

UK Search Report—IPO for Corresponding Application No. GB 0909985.4, dated Oct. 8, 2009.

* cited by examiner

*Primary Examiner* — Nicholas Lucchesi
*Assistant Examiner* — Aarti B Berdichevsky
(74) *Attorney, Agent, or Firm* — Paul D. Bianco; Martin Fleit; Fleit Gibbons Gutman Bongini & Bianco PL

(57) ABSTRACT

A syringe hub comprises a hub body which is engagable with a syringe body, a needle held by the hub body, a movable bung element within a flow passage of the hub body, and at least one fixed engagement element which extends laterally to the longitudinal extent of the flow passage and which is non-releasably engagable with the bung element to block a flow path defined by the hub body and the needle. The movable bung element including a cap element which extends laterally to the longitudinal extent of the flow passage and a splayable engagement element which extends from the cap element. The splayable engagement element includes a plurality of legs. A syringe which has a syringe body and the said syringe hub is also provided.

18 Claims, 4 Drawing Sheets

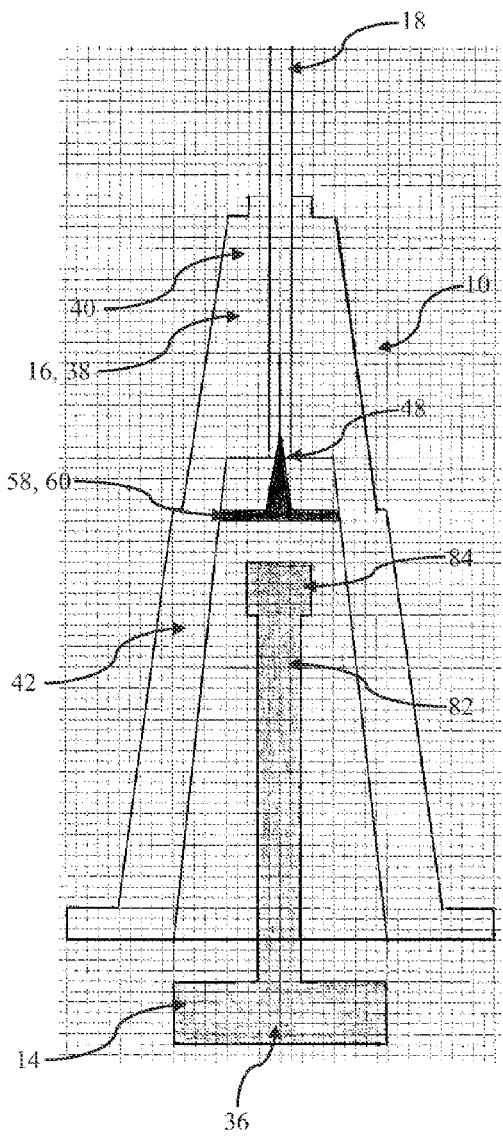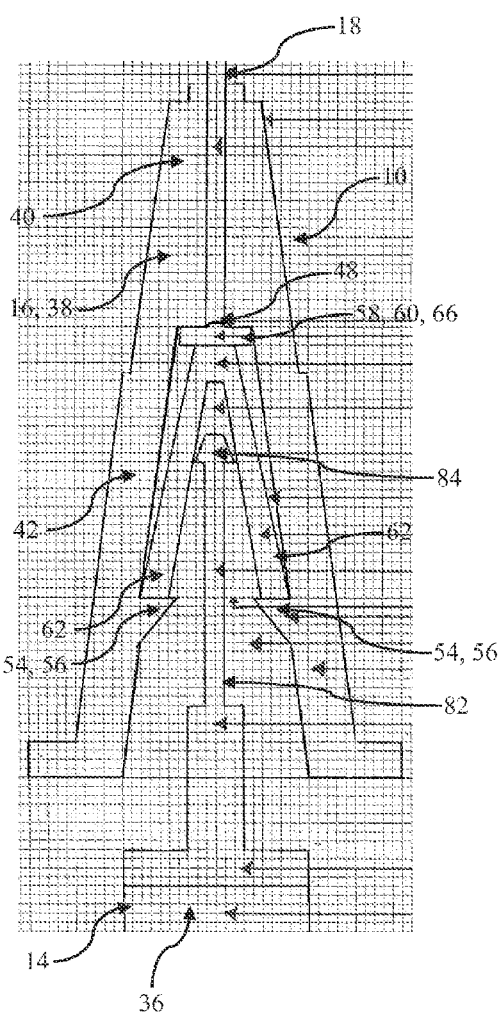
Fig. 6
Fig. 5

SYRINGE HUB

The present invention relates to an auto-disposable syringe hub which carries a needle, and to a syringe having such a hub.

BACKGROUND OF THE INVENTION

Many diseases are transmitted by pathogens introduced into the body via previously used and contaminated needles and syringes. An auto-disposable or auto-destructible syringe is known from U.S. Pat. No. 6,368,306B1, and whilst this arrangement goes some way to preventing cross-contamination and infection, it only disables the syringe body or barrel. Many syringes have removable needles, and thus a contaminated needle can simply be swapped to a new syringe body and reused.

The present invention seeks to provide a solution to this problem.

SUMMARY OF THE INVENTION

According to a first aspect of the present invention, there is provided a syringe hub comprising a hub body which is engagable with a syringe body, a needle held by the hub body, a movable bung element within a flow passage of the hub body, at least one fixed engagement element which extends laterally to the longitudinal extent of the flow passage and which is non-releasably engagable with the bung element to block a flow path defined by the hub body and the needle, wherein the movable bung element includes a cap element which extends laterally to the longitudinal extent of the flow passage and a splayable engagement element which extends from the cap element, the splayable engagement element including a plurality of legs.

Preferably, the syringe hub is auto-disposable, the syringe hub being automatically renderable inoperable for repeat use.

According to a second aspect of the present invention, there is provided A syringe comprising : a syringe body; a piston assembly slidable within the syringe body; and a syringe hub including a hub body which is engagable with the syringe body, a needle held by the hub body, a movable bung element within a flow passage of the hub body, and at least one fixed engagement element which extends laterally to the longitudinal extent of the flow passage and which is non-releasably engagable with the bung element, wherein the movable bung element includes a cap element which extends laterally to the longitudinal extent of the flow passage and a splayable engagement element which extends from the cap element, the splayable engagement element including a plurality of legs; and wherein the bung element in the hub body is movable by the piston assembly to block a flow path defined by the hub body and the needle.

The present invention will now be more particularly described, by way of example only, with reference to the accompanying drawings.

BRIEF DESCRIPTION OF THE DRAWINGS

FIG. 5 shows a fourth embodiment of the syringe hub and part of a piston assembly; and FIG. 6 shows a fifth embodiment of the syringe hub and part of a piston assembly.

DESCRIPTION OF THE PREFERRED EMBODIMENTS

Figure 1:
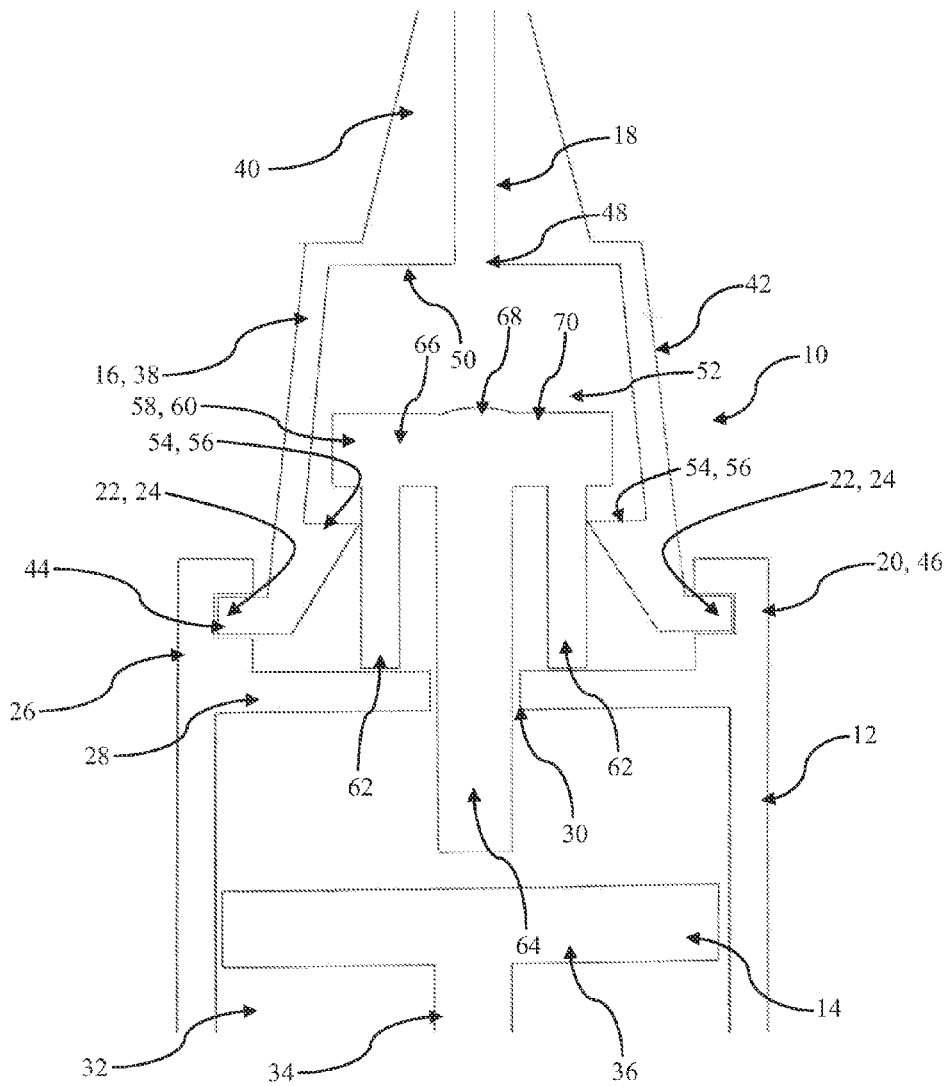
FIG. 1 shows a first embodiment of a syringe hub engaged with a syringe body, and shown with a movable bung element in a flow condition.
Figure 2:
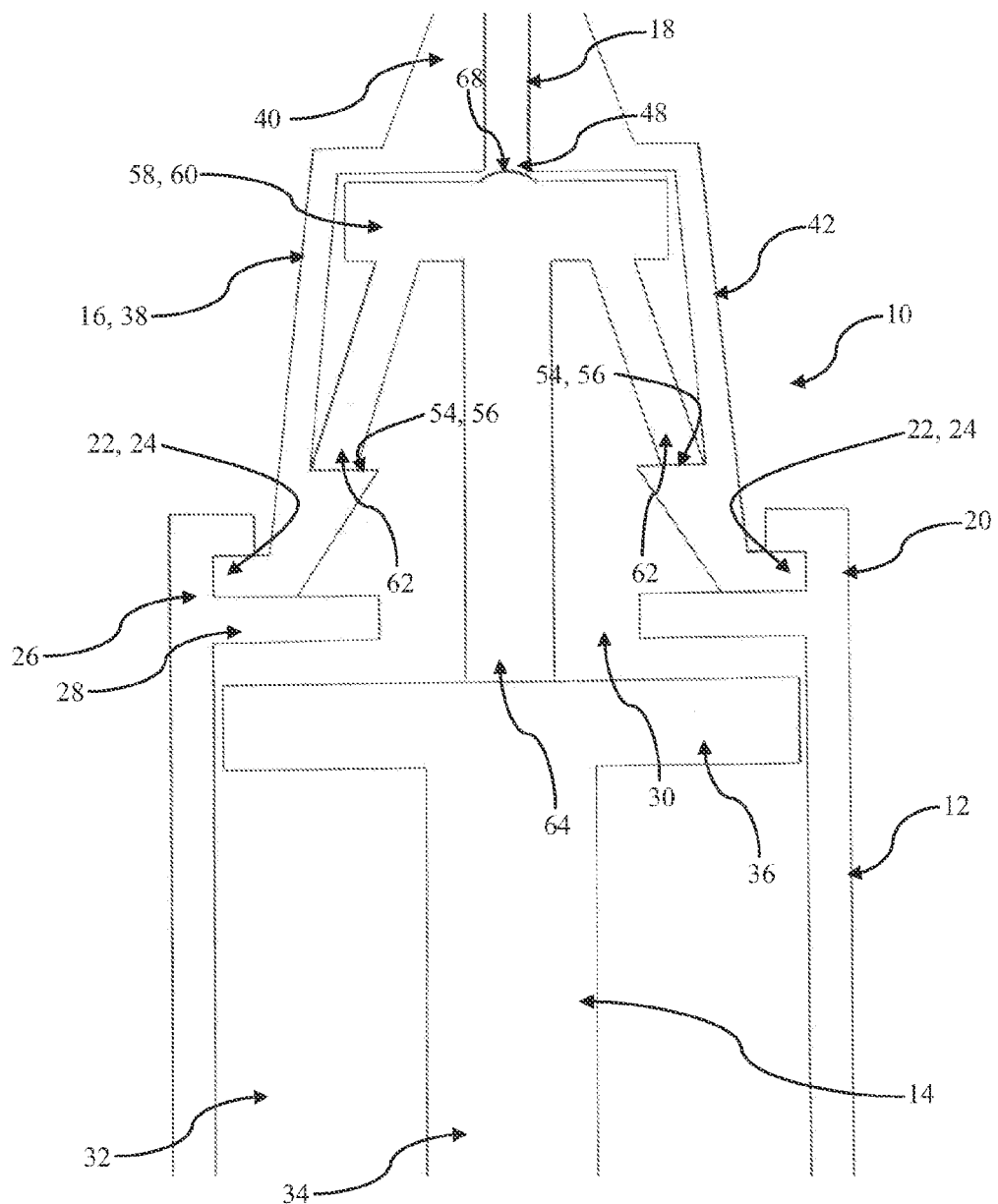
FIG. 2 shows the syringe hub and syringe body with the bung element moved to a stop condition.

Referring firstly to FIGS. 1 and 2 of the drawings, there is shown a first embodiment of a syringe 10 which comprises a syringe body 12, a piston assembly 14 slidable within the syringe body 12, and a syringe hub 16 which permanently holds a needle 18.

The syringe body 12 is typically plastics and generally cylindrical along the majority of its longitudinal extent. Hub engaging means 20 is integrally provided at one end of the syringe body 12 for liquid-tightly engaging the syringe hub 16. In this case, the hub engaging means 20 comprises a circumferentially extending inwardly facing annular channel element 22 in which a portion of the syringe hub 16 can locate for liquid-tight engagement. The channel element 22 may be continuous or discontinuous. In this latter case, the channel element 22 may be in the form of a plurality of spaced channel portions 24.

A hub end 26 of the syringe body 12 includes a, preferably integral, syringe end wall 28 having a syringe flow aperture 30 centrally provided therethrough.

The piston assembly 14 is slidably received in the cylindrical bore 32 of the syringe body 12. A surface of the cylindrical bore 32, in this embodiment, is entirely smooth. The piston assembly 14 includes a rigid plunger shaft 34 and an elastomeric plunger head 36 for forcing liquid within the syringe body 12 out through the syringe flow aperture 30.

The syringe hub 16 has a generally frusto-conical hub body 38 with the needle 18 being fixedly carried at the distal end thereof In this embodiment, an outer surface of the hub body 38 is stepped to define two frusto-conical portions 40, 42. A distal frusto-conical portion 40 supports the needle 18, and the proximal frusto-conical portion 42 includes at least one outwardly extending flange 44 at or adjacent to the syringe end 46 for engagement with the annular channel element 22 of the hub engaging means 20.

An interior surface of the hub body 38 is also preferably substantially frusto-conical. A needle opening 48 to the lumen of the needle 18 is provided centrally in a hub end wall 50 of the hub body 38. The interior surface and the hub end wall together define an interior cavity 52 for receiving liquid from the needle 18 during drawing and from the syringe body 12 during discharge.

The interior cavity 52 of the hub body 38 is integrally formed with at least one inwardly projecting ramped shoulder element 54. The shoulder element 54 may extend in a circumferential direction continuously around the interior cavity 52, or may be discontinuous. In this latter case, the shoulder element 54 may be formed by a plurality of spaced shoulder portions 56.

Although an inwardly projecting shoulder element 54 is suggested, any suitable bung engagement means can be considered. For example, a channel or recess can be formed in the interior surface of the hub body 38, instead of utilising the shoulder element.

Although the interior cavity 52 of the hub body 38 is substantially frusto-conical thus forming a flow passage to the needle 18, the interior cavity may be cylindrical.

The syringe hub 16 is also provided with a movable bung element 58, which for example is formed of rubber or other relatively hard elastomeric material. The bung element 58 comprises a cap portion 60, at least one splayable engagement element 62 which extends transversely to the cap portion 60, and a bung shaft 64 which extends centrally from the cap portion 60. The cap portion 60 has generally flat or planar cap body 66 having a dimension which approaches but preferably does not meet the frusto-conical interior surface of the interior cavity 52. A perimeter edge or edges of the cap body 66 extend over the innermost edge or edges of the shoulder element 54 to prevent or inhibit unintentional removal of the bung element 58 prior to use.

The cap portion 60 also includes a stopper element 68 substantially centrally on a distal facing major surface 70. The stopper element 68 is adapted to be at least in part insertable into the needle opening 48 in the hub end wall 50 of the hub body 38. In this embodiment, the stopper element 68 is a slightly domed projecting mound integrally formed as one-piece with the cap body 66.

In a flow condition, the splayable engagement element 62 is received radially inwards of the shoulder element 54. The splayable engagement element 62 may be independent legs or a skirt. In either case, one or more bung flow apertures may be provided therethrough.

The bung shaft 64 is rigid enough to be urgable by the piston assembly 14 in order to move the bung element 58 in the hub body 38. The bung shaft 64 has a longitudinal extent which is sufficient to project through the syringe flow aperture 30 of the syringe body 12, and the bung shaft 64 itself may also include one or more shaft flow apertures.

In use, the syringe hub 16 is engaged with the syringe body 12 such that the bung shaft 64 of the bung element 58 projects into the interior of the syringe body 12. The free end or ends of the engagement element 62 abut and frictionally engage an outer surface of the syringe body adjacent to the aperture 30. The piston assembly 14 is used to draw liquid into the syringe body 12 via the needle 18 and the interior cavity 52 of the hub body 38. Flow during drawing is largely unrestricted due to the bung flow apertures in the bung element 58 and the shaft flow apertures in the bung shaft 64. The engagement element 62 is resilient enough not to collapse under the pressure of liquid being indrawn, and the inner edges of the shoulder element 54 support the longitudinal extent of the engagement element 62, preventing outward buckling.

The piston assembly 14 can then be used to expel the drawn liquid from the needle 18 by moving the plunger head 36 via the plunger shaft 34 towards the syringe end wall 28 of the syringe body 12. The bung element 58 is held in or substantially in place during liquid flow, typically by frictional engagement between the engagement element 62 and the inner edge or edges of the shoulder element 54. As the syringe end wall 28 is approached, the plunger head 36 contacts the free end of the bung shaft 64 of the bung element 58 and urges the bung element 58 towards the needle opening 48. As the engagement element 62 clears the shoulder element 54, it splays outwards preventing return. At the same time, the cap portion 60 contacts the hub end wall 50, causing the stopper element 68 to at least partially enter and thus block the needle opening 48.

Due to the engagement element 62 acting on the shoulder element 54, the stopper element 68 is held tightly over the needle opening 48 and liquid cannot be again drawn back into the syringe body 12. The syringe hub 16 utilising the movable bung element 58 thus provides a single shot syringe 10 and renders a needle 18 held thereby non-reusable.

Figure 3:
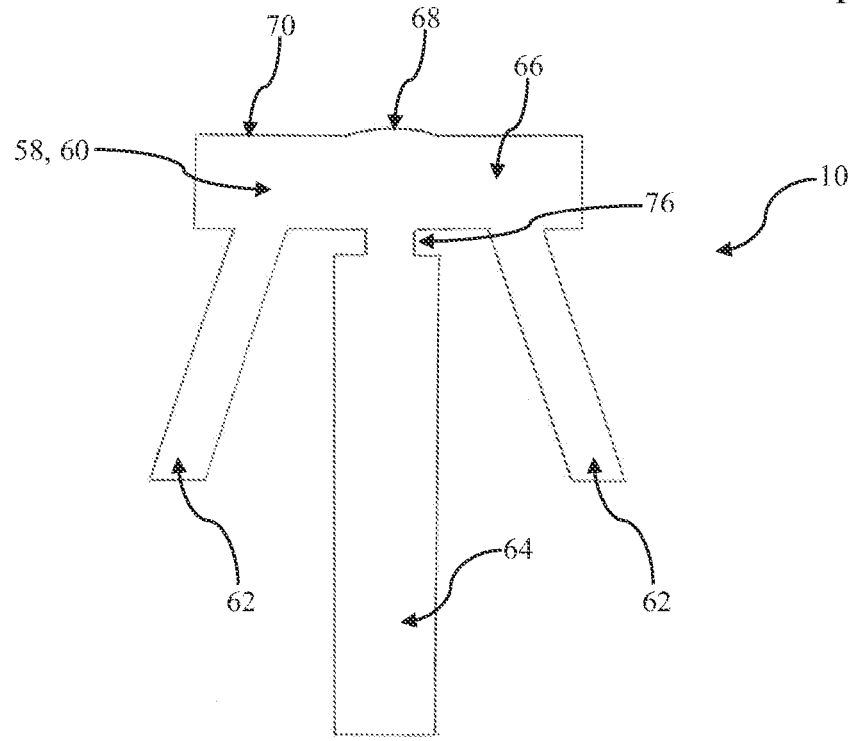
FIG. 3 shows a second embodiment of the movable bung element.

Referring to FIG. 3, a second embodiment of a syringe 10 is now briefly described. The only difference to that of the first embodiment relates to the movable bung element 58, and therefore the other features are omitted. Like references refer to like parts, and thus further detailed description is not provided.

It is considered that the syringe hub 16 could be removed from the syringe body 12, thus allowing access to at least the bung shaft 64 of the movable bung element 58 even when in the stop condition with the engagement element 62 braced against the shoulder element 54. To this end, the bung shaft 64 may include a frangible or weakened portion 76 so that if forcibly withdrawn from the interior cavity 52 of the hub body 38, it simply breaks free leaving the cap portion 60 and engagement element 62 in place.

Figure 4:
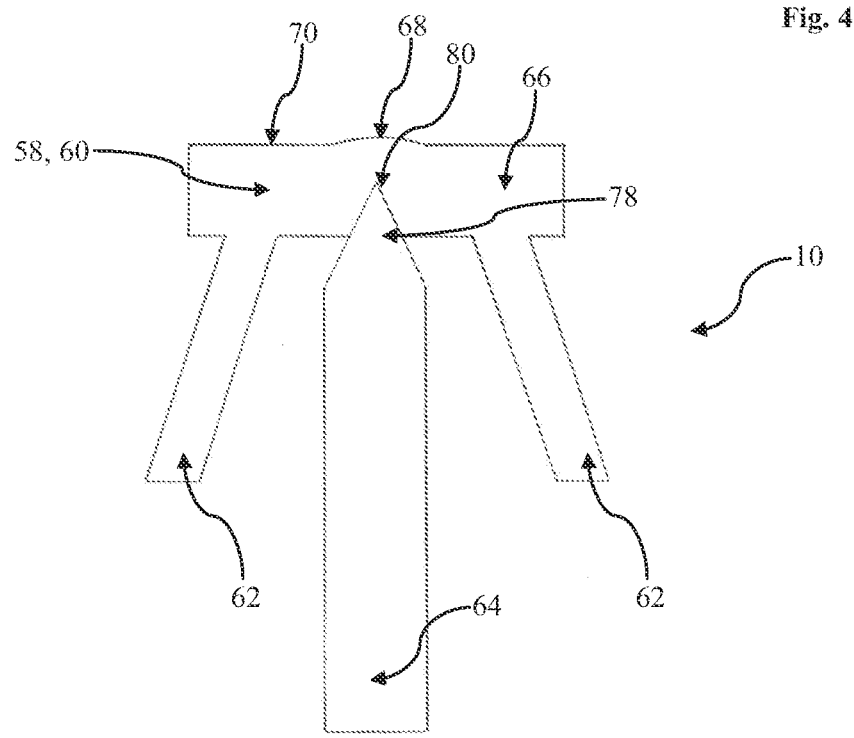
FIG. 4 shows a third embodiment of the movable bung element.

Referring to FIG. 4, a third embodiment of a syringe 10 is now briefly described. This embodiment is similar in all respects to that of the first embodiment, with the only difference relating to the movable bung element 58. Therefore, the other features are omitted. Like references refer to like parts, and further detailed description is dispensed with.

Instead of providing a frangible shaft, as in the second embodiment, the bung shaft 64 may simply be able to be pulled free of the cap portion 60. To this end, an end of the bung shaft 64 may simply be retained in the cap portion 60 as a projecting plug 78, and as shown the plug end 80 may be tapered. This allows the bung element 58 to be pushed via the bung shaft 64 into place whereby it stops a flow to and from the needle 18, but if pulled out of the hub body 38, simply detaches leaving the cap portion 60 and engagement element 62 behind and in place.

Referring to FIG. 5, a fourth embodiment of a syringe 10 is shown. Again, similar references relate to parts which are similar to those described above, and further detailed description is omitted.

In this case, the piston assembly 14 carries a bung urging shaft 82 which projects from a distal end of the plunger head 36 and through the syringe flow aperture 30 in the syringe end wall 28. The lateral extent of the bung urging shaft 82 is significantly less than that of the syringe flow aperture 30, thereby enabling substantially unrestricted flow.

The hub body 38 and movable bung element 58 are substantially as described above, except without the onboard bung shaft 64.

With the hub body 38 attached to the syringe body 12, a projecting end 84 of the bung urging shaft 82 approaches and contacts the cap portion 60 of the bung element 58. As liquid is discharged through the needle 18 by the pressing movement of the piston assembly 14, the bung urging shaft 82 carried by the plunger head 36 moves the bung element 58 towards the hub end wall 50 of the hub body 38. The engagement element 62 thus slides over the shoulder element 54 and splays outwards, preventing return, as the cap portion 60 contacts the end wall and blocks the needle opening 48.

The bung urging shaft 82 may again be frangible to prevent or inhibit removal and reuse. To aid this, the projecting end 84 of the bung urging shaft 82 may include a head 86 which may be dimensioned to contact the shoulder element 54 on attempted removal, thus causing fracture and/or breakage of the bung urging shaft 82.

Referring to FIG. 6, a fifth embodiment of the syringe 10 is shown, which comprises a modified syringe hub 16 and bung element 58. Again, like references refer to like parts and further detailed description of those parts is omitted.

In this embodiment, the stopper element 68 of the cap portion 60 is shaped to be conical or substantially conical, providing the appearance of a spike. In use, the spike is thus moved into tight wedging engagement within the needle opening 48 and/or the lumen of the needle 18.

The spike-like stopper element 68 can thus also form the engagement element 62 of the syringe hub 16, dispensing with the need for a skirt or legs which extend from the cap portion 60. However, the skirt or legs can be utilised as necessity dictates.

The shoulder element 54 of the bung engagement means may also be dispensed with. The interior, preferably frusto-conical, side surface of the hub body 38 can act as the engagement means, whereby the outer edge or edges of the cap portion 60 are forced into wedging engagement therewith as the cap portion 60 is moved by the bung shaft 64 of the bung element 58 or the bung urging shaft 82 of the piston assembly 14.

The shoulder element can of course be provided, and this may be positioned so that the perimeter edge of the cap portion slides thereover during urging, thereby preventing or limiting return.

The width of the cap portion of the bung element is such that it preferably overlies or overlaps the aperture defined by the inner edges of the shoulder element to prevent or limit extraction. The bung element thus may be formed in situ within the hub body, or may be push fit inserted due to its inherent flexibility. Alternatively, the shoulder element may be non-continuous and the overlapping parts of the cap portion may be discreet projections thereby allowing alignment with the gaps or openings in the shoulder element to permit insertion.

It is thus possible to provide an auto-disposable syringe hub which utilises a bung element, thus automatically blocking a flow path defined by the hub body and the needle following a single use. This prevents repeat use of the needle carried by the hub body and thus reduces the likelihood of cross-contamination and transmission of disease. The syringe hub can be provided as one-piece with the syringe body, or can be separate and engagable therewith. The syringe hub and the bung element can operate with a generally standard syringe body and piston assembly, or can be utilised with a specific piston assembly carrying a bung urging shaft. The bung urging shaft carried by the bung element or the piston assembly is advantageously detachable to prevent or inhibit removal of, in particular, the bung element when in a stop condition. The bung element is only activated by the plunger assembly acting directly on the shaft.

The embodiments described above are provided by way of examples only, and various other modifications will be apparent to persons skilled in the field without departing from the scope of the invention as defined by the appended claims.

What is claimed is:

1. A syringe hub comprising a hub body which is removably engageable with a syringe body, a needle fixedly held by the hub body, a moveable bung element within a flow passage of the hub body, the moveable bung element including a cap element which extends laterally to a longitudinal extent of the flow passage and a stopper element configured for at least partial insertion into a lumen of the needle, a splayable engagement element extending from the cap element, the splayable engagement including a plurality of legs, and at least one fixed engagement element which extends laterally to the longitudinal extent of the flow passage and includes at least one shoulder element integrally formed with an interior cavity of the hub body and inwardly projecting into the flow passage; wherein in a stop configuration each leg of the plurality of legs non-releaseably engages an inwardly projecting shoulder element such that the stopper element is inserted into the lumen of the needle to block a flow path defined by the hub body and the needle.

2. A syringe hub as claimed in claim 1, wherein the syringe hub is auto-disposable, the syringe hub being automatically renderable inoperable for repeat use.

3. A syringe hub as claimed in claim 1, wherein the moveable bung element is positioned such that the stopper element is moveable to block an opening of the lumen of the needle.

4. A syringe hub as claimed in claim 1, wherein the cap element includes at least one flow aperture therethrough.

5. A syringe hub as claimed in claim 1, wherein the legs are independently moveable relative to each other.

6. A syringe hub as claimed in claim 1, wherein the moveable bung element is flexible.

7. A syringe hub as claimed in claim 1, wherein the hub body includes a frusto-conical or substantially frusto-conical outer surface.

8. A syringe hub as claimed in claim 1, wherein at least a portion of the flow passage within the hub body is frusto-conical.

9. A syringe hub as claimed in claim 1, further comprising a connector for connecting the hub body to a syringe body, the connector including an outturned flange at or adjacent to one end of the hub body engageable with the syringe body.

10. A syringe hub as claimed in claim 1, further comprising a shaft for moving the bung element within the hub body.

11. A syringe hub as claimed in claim 10, wherein the shaft is engaged with the bung element and when in a flow position projects from the hub body.

12. A syringe hub as claimed in claim 11, wherein the shaft is frangible.

13. A syringe hub as claimed in claim 11, wherein the shaft is disconnectable from the bung element.

14. A syringe comprising:
a syringe body;
a piston assembly slidable within the syringe body; and
a syringe hub including a hub body which is removably engageable with the syringe body, a needle fixedly held by the hub body, a moveable bung element within a flow passage of the hub body, the moveable bung element including a cap element which extends laterally to a longitudinal extent of the flow passage and a stopper element configured for at least partial insertion into a lumen of the needle, a splayable engagement element extending from the cap element, the splayable engagement including a plurality of legs, and at least one fixed engagement element which extends laterally to the longitudinal extent of the flow passage and includes at least one shoulder element integrally formed with an interior cavity of the hub body and inwardly projecting into the flow passage; wherein in a stop configuration each leg of the plurality of legs non-releaseably engages an inwardly projecting shoulder element and the bung element is movable by the piston assembly such that the stopper element is inserted into the lumen of the needle to block a flow path defined by the hub body and the needle.

15. A syringe as claimed in claim 14, wherein the syringe is auto-disposable, the syringe hub automatically rendering the syringe inoperable for repeated use.

16. A syringe as claimed in claim 14, wherein the bung element in the hub body is moved by the piston assembly to block the flow path as the piston assembly reaches or nears a hub end of the syringe body.

17. A syringe as claimed in claim 14, wherein the piston assembly includes a disconnectable shaft for moving the bung element within the hub body.

18. A syringe as claimed in claim 17, wherein the disconnectable shaft is frangible.

* * * * *